United States Patent [19]

Leonard et al.

[11] Patent Number: 4,695,615
[45] Date of Patent: * Sep. 22, 1987

[54] INSTANT ADHESIVE COMPOSITION UTILIZING MIXED FUNCTIONALITY CALIXARENES AS ACCELERATORS

[75] Inventors: Raymond G. Leonard, Co. Kildare; Stephen J. Harris, Dublin, both of Ireland

[73] Assignee: Loctite (Ireland) Limited, Tallaght, Ireland

[ * ] Notice: The portion of the term of this patent subsequent to Dec. 3, 2002 has been disclaimed.

[21] Appl. No.: 825,012

[22] Filed: Jan. 31, 1986

Related U.S. Application Data

[60] Continuation-in-part of Ser. No. 717,251, Mar. 28, 1985, Pat. No. 4,642,362, and a continuation-in-part of Ser. No. 776,536, Sep. 16, 1985, Pat. No. 4,636,539, which is a division of Ser. No. 673,621, Nov. 21, 1984, Pat. No. 4,556,700, and a continuation-in-part of Ser. No. 575,257, Jan. 30, 1984, abandoned.

[51] Int. Cl.[4] .............................................. C08F 20/34
[52] U.S. Cl. ..................................... 526/194; 526/208; 526/209
[58] Field of Search ....................... 526/194, 208, 209

[56] References Cited

U.S. PATENT DOCUMENTS

| | | | |
|---|---|---|---|
| 4,042,442 | 8/1977 | Dombroski et al. | 156/310 |
| 4,170,585 | 10/1979 | Motegi et al. | 260/33.2 |
| 4,171,416 | 10/1979 | Motegi et al. | 526/245 |
| 4,377,490 | 3/1983 | Shiraishi et al. | 252/188.3 |
| 4,386,193 | 5/1983 | Reich et al. | 526/298 |
| 4,393,183 | 7/1983 | Kimura et al. | 526/245 |
| 4,425,471 | 1/1984 | Millet | 526/298 |
| 4,556,700 | 3/1985 | Harris et al. | 526/209 |

FOREIGN PATENT DOCUMENTS 2069512 8/1981 United Kingdom .

OTHER PUBLICATIONS

Gutche, Acc. Chem. Res. 16 161-170 (1983).
Ungaro, et al., "New Ionizable Ligands from p-t-butyl-calix[4]arene", J. Inclusion Phenomena., 2 199-206 (1984).
Chem. Abst. 97 145913n (1982).
Chem. Abst. 97 110995p (1982).

*Primary Examiner*—Paul R. Michl
*Attorney, Agent, or Firm*—Walter J. Steinkraus; Eugene F. Miller

[57] ABSTRACT

Cyanoacrylate adhesive compositions which employ calixarene compounds as additives give substantially reduced fixture and cure times on de-activating substrates such as wood. The calixarene compounds are preferable employed at levels of about 0.1-2% by weight of the composition.

The calixarene compounds particularly useful in this invention may be represented by the formula:

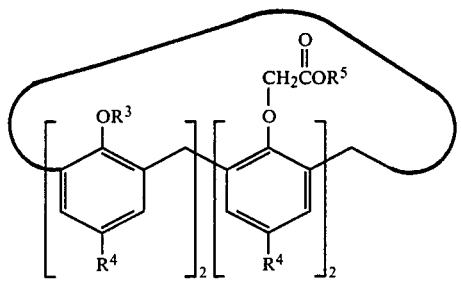

where $R^3$ is H, $-CH_2C(=O)OH$, $CH_2C(=O)OR^6$, $-C(=O)R^8$, hydrocarbyl, or trihydrocarbylsilyl or the two $R^3$ groups together form a divalent hydrocarbyl or oxygen interrupted hydrocarbyl group; $R^4$ is H or hydrocarbyl; $R^5$ is hydrocarbyl, hydrocarbyl interrupted by one or more oxygen atoms, or hydrocarbyl substituted with halo, nitro, or oxo groups; $R^6$ is as defined for $R^5$ but different therefrom; and $R^8$ is as defined for $R^5$ but the same or different therefrom.

11 Claims, No Drawings

INSTANT ADHESIVE COMPOSITION UTILIZING MIXED FUNCTIONALITY CALIXARENES AS ACCELERATORS

This application is a continuation-in-part of copending Ser. No. 717,251 of Mar. 28, 1985, now U.S. Pat. No. 4,642,362, and 776,536 of Sept. 16, 1985 now U.S. Pat. No. 4,636,539 which is a division of Ser. No. 673,621 of Nov. 21, 1984, now U.S. Pat. No. 4,556,700, which is a continuation-in-part of Ser. No. 575,257 of Jan. 30, 1984, abandoned.

BACKGROUND OF THE INVENTION

In DE-OS No. 2,816,836, dated Oct. 26, 1978 there are described cyanoacrylate adhesive compositions which employ crown ethers as polymerization accelerators. Such compositions are useful for bonding acidic surfaces such as wood which inhibit cyanoacrylate polymerization.

Crown ethers, however, are known to be very toxic, the reported effects of exposure including damage to the central nervous system and testicular atrophy. Leong, B. K. J., Chem. Eng. News, 53, 5(1975). Furthermore, such accelerators are reportedly very difficult to synthesize, supplying the desired product in only low yields because of the tendency to produce intermolecular linkages. Accordingly, there is a need for alternative cyanoacrylate accelerators suitable for wood bonding applicators.

In U.S. Pat. No. 4,170,585, there are described cyanoacrylate compositions in which certain polyethylene glycols or poly(ethyleneoxy) functional surfactants act as wood bonding accelerators. Such compounds, however, have the reported disadvantage that they tend to contain water and other difficult to remove substances which spontaneously initiate polymerization of the cyanoacrylate monomer.

U.S. Pat. No. 4,377,490 discloses mixtures of aromatic and aliphatic polyols and polyethers said to improve initial strength of cyanoacrylate wood bonding products.

U.S. Pat. No. 4,386,193 discloses certain 3 or 4 arm polyol podand compounds as alternatives to crown-ether accelerators.

Japan Kokai Tokkyo Koho No. 82-70171, suggests the use of certain polyorganosiloxane compounds which include polyether substituents as additives for wood bonding cyanoacrylate compositions.

Chem. Abstracts, 97 145913n reports the use of a hydroxy-terminated poly(dimethylsiloxane) in fast bonding cyanoacrylate compositions.

DE-OS No. 3,006,071 discloses certain furan derivatives as co-accelerators with crown ethers in cyanoacrylate compositions.

DISCLOSURE OF THE INVENTION

The present invention is a new cyanoacrylate composition for bonding wood and other de-activating surfaces such as leather, ceramic, plastics and metals with chromate threated or acidic oxide surfaces. The inventive compositions are standard cyanoacrylate adhesive formulations to which have been added, as accelerators, certain calixarene compounds stable to cyanoacrylate monomers. The calixarene compounds are employed in amounts conventional for cyanoacrylate accelerators, preferably at levels between about 0.1% and 2% by weight of the composition.

Calixarene compounds disclosed in U.S. No. 4,556,700 as useful as cyanoacrylate accelerators may be represented by the formula:

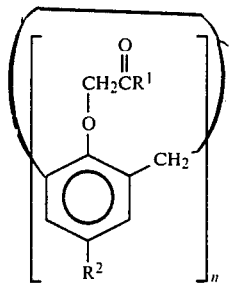

where $R^1$ is alkyl, alkoxy, substituted alkyl or substituted alkoxy; $R^2$ is H or alkyl; and $n=4$, 6, or 8.

Other compounds which show some activity as cyanoacrylate accelerators include carboxylic acid esters of the phenolic calixarene compounds, such as the hexa- and octa- propanoate esters of the respective hexamer and octomer, and ethers such as the tetramer tetramethyl ether. Such compounds have only marginal utility, however, because that only cut polymerization time by about 50%.

Another class of calixarene compounds which has now been discovered to be highly useful as cyanoacrylate compositions are tetramers with mixed functionality. These compounds may be represented by the formula:

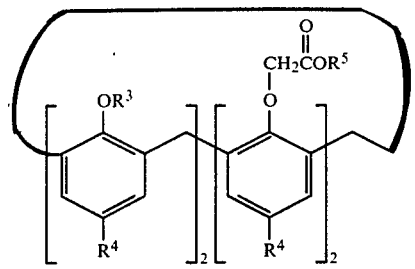

where $R^3$ is H, $-CH_2C(=O)OH$, $-CH_2C(=O)OR^6$, $-C(=O)R^8$, hydrocarbyl, or trihydrocarbylsilyl or the two $R^3$ groups together form a divalent hydrocarbyl or oxygen interrupted hydrocarbyl group; $R^4$ is H or hydrocarbyl; $R^5$ is hydrocarbyl, hydrocarbyl interrupted by one or more oxygen atoms, or hydrocarbyl substituted with halo, oxo, or nitro groups; $R^6$ is as defined for $R^5$ but is a different group therefrom; and $R^8$ is as defined for $R^5$ but may be the same or different therefrom. Examples for suitable $R^3$ and $R^4$ hydrocarbyl groups include alkyl such a methyl, ethyl, propyl, t-butyl, hexyl or nonyl; alkenyl such as allyl; and phenyl. A suitable trihydrocarbylsily group is trimethylsilyl. $R^4$ is preferably H or t-butyl. Specific examples for $R^5$ are a methyl group, an ethyl group, an n-propyl group, an isopropyl group, an n-butyl group, an isobutyl group, a pentyl group, a hexyl group, an allyl group, a methallyl group, a crotyl group, a propargyl group, a cyclohexyl group, a benzyl group, a phenyl group, a cresyl group, a 2-chloroethyl group, a 3-chloropropyl group, a 2-chlorobutyl group, a trifluoroethyl group, a 2-methoxyethyl group, a 3-methoxybutyl group and a 2-ethoxyethyl group.

The α-cyanoacrylate-type adhesive composition of this invention as described above contains an α-cyanoacrylate monomer of the formula:

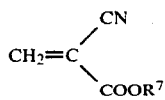

wherein $R^7$ represents a straight chain or branched chain alkyl group having 1 to 12 carbon atoms (which may be substituted with a substituent such as a halogen atom or an alkoxy group) a straight chain or branched chain alkenyl group having 2 to 12 carbon atoms, a straight chain or branched chain alkynyl group having 2 to 12 carbon atoms, a cycloalkyl group, an aralkyl group or an aryl group. Specific examples of the groups for $R^7$ are a methyl group, an ethyl group, an n-propyl group, an isopropyl group, an n-butyl group, an isobutyl group, a pentyl group, a hexyl group, an allyl group, a methallyl group, a crotyl group, a propargyl group, a cyclohexyl group, a benzyl group, a phenyl group, a cresyl group, a 2-chloroethyl group, a 3-chloropropyl group, a 2-chlorobutyl group, a trifluoroethyl group, a 2-methoxyethyl group, a 3-methoxybutyl group and a 2-ethoxyethyl group. Ethyl cyanoacrylate is the preferred monomer for use in the inventive compositions.

A single α-cyanoacrylate monomer or a mixture of two or more of these α-cyanoacrylate monomers can be used. Generally, the above α-cyanoacrylate monomer alone is not sufficient as an adhesive, and the components set forth below are sometimes added.

(1) An anionic polymerization inhibitor
(2) A radical polymerization inhibitor
(3) A thickener
(4) Special additives such as plasticizers and heat stabilizers
(5) Perfumes, dyes, pigments, etc.

A suitable amount of the α-cyanoacrylate monomer present in the adhesive composition is about 80 to 99.9% by weight, preferably 90 to 99.9% by weight, based on the total weight of the adhesive composition.

An anionic polymerization inhibitor is added to the α-cyanoacrylate-type adhesive composition, e.g., in an amount of about 1 to 1000 ppm based on the total weight of the adhesive composition, to increase the stability of the adhesive composition during storage, and examples of known inhibitors are sulfur dioxide, aromatic sulfonic acids, aliphatic sulfonic acids, sultones, and carbon dioxide.

Suitable examples of radical polymerization inhibitors include, for example, hydroquinone and hydroquinone monomethyl ether. A radical polymerization inhibitor is added, e.g., in amount of about 1 to 5000 ppm based on the total weight of the adhesive composition, for the purpose of capturing radicals which are formed by light during storage.

A thickener is added to increase the viscosity of the α-cyanoacrylate-type adhesive composition. The α-cyanoacrylate monomer generally has a low viscosity of about several centipoises, and therefore, the adhesive penetrates into porous materials such as wood and leather or adherends having a rough surface. Thus, good adhesion strengths are difficult to obtain. Various polymers can be used as thickeners, and examples, include poly(methyl methacrylate), methacrylate-type copolymers, acrylic rubbers, cellulose derivatives, polyvinyl acetate and poly(α-cyanoacrylate). A suitable amount of thickener is generally about 20% by weight or less based on the total weight of the adhesive composition.

As disclosed in U.S. Pat. No. 4,477,607, certain fumed silica fillers treted with polydialkylsiloxanes or trialkylsilanes may also be usefully employed as cyanoacrylate thickeners.

The plasticizers, perfumes, dyes, pigments, etc., may be added depending on use purposes in amounts which do not adversely affect the stability of the α-cyanoacrylate monomer. The use of such additives is wihin the skill of those practicing in the cyanoacrylate adhesive art and need not be detailed herein.

Calixarene compounds are known and may be readily synthesized by methods described in U.S. Pat. No. 4,556,700 and in C. Gutsche, Acc. Chem. Res., 16, 161-170 (1983), and references cited therein, the appropriate disclosures of which are incorporated herein by reference. Synthesis methods for the calixarene compounds of the invention are exemplified in Examples 1-4 herein and in Journal of Inclusion Phenomena 2 199-206 (1984) D. Reidel Publishing Company.

The invention may be further understood with reference to the following non-limiting examples.

EXAMPLE 1

Preparation of Dietherified Calix(4)arene

A mixture of 1.62 g of 5,11,17,23-tetra-tert-butyl calix(4)arene, 2.0 g of ethyl bromoacetate, 2.07 g of anhydrous potassium carbonate, and 20 milliliters of dried DMSO was stirred for 48 hours under nitrogen at room temperature. At the end of this time, the mixture was poured into 200 milliliters of a 10% solution of aqueous hydrochloric acid. The precipitated off-white solid was filtered and washed twice with distilled water to yield 2.0 g of crude product. Recrystallization of this material from hot ethanol gave 1.64 g of a crystalline product (M.Pt.=173°–175° C.) which was characterized by i.r. and n.m.r. spectroscopy as the dietherified calix(4)arene:

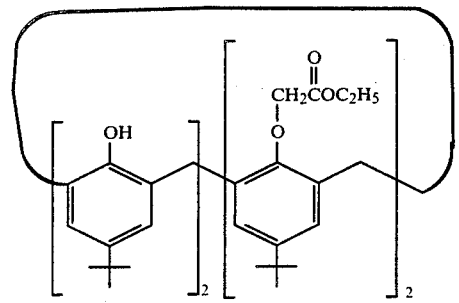

Elemental analysis: (Calc'd for $C_{52}H_{68}O_8$, C: 76.04, H: 8.36 O: 15.59; Found, C: 75.59, H: 8.31, O: 16.03).

EXAMPLE 2

A mixture of 1.65 g of dietherified calix(4)arene prepared as in Example 1, 0.096 g of sodium hydride, and 25 milliliters of dry THF was refluxed for 21 hours under nitrogen and then 0.585 g of allyl bromide was added dropwise over 10 minutes. The entire mixture was then refluxed for a further one hour, cooled and poured into 150 milliliters of a 10% solution of aqueous hydrochloric acid. The precipitated off-white solid was filtered and dried at 50° C. overnight. Recrystallization of this material from hot ethanol gave 1.5 g of a crystalline product (M.Pt.=167°-168° C.) which was characterized by i.r. and n.m.r. spectroscopy as a diallyl calix-(4)arene:

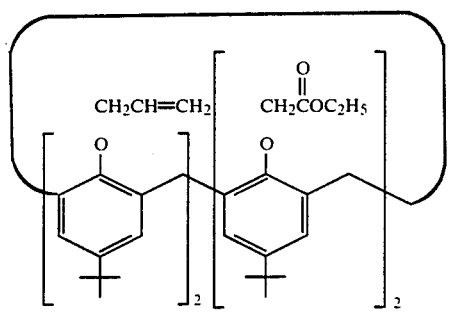

Elemental analysis: (Calc'd for $C_{58}H_{76}O_8$, C: 77.28, H: 8.52, O: 14.20; Found, C: 76.87, H: 8.35, O: 13.82).

EXAMPLE 3

Preparation of Calix(4)arene Diallylacetate Ester

A mixture of 1.9 g of dietherified calix(4)arene prepared as in Example 1, 1.04 g of allyl bromoacetate, and 1.0 g anhydrous potassium carbonate was heated to 130° C. under nitrogen with stirring for 30 minutes. The resulting solid mass was cooled and added to 100 milliliters of a 10% solution of aqueous hydrochloric acid. The undissolved solid was filtered, washed twice with distilled water and dried overnight at 55° C. to give 2.7 g of crude product. Recrystallization of this material from hot ethanol yielded 2.1 g of a crystalline product (M.Pt.=115° C.) which was characterised by i.r. and n.m.r. spectroscopy as a diallyl ester of calix(4)arene.

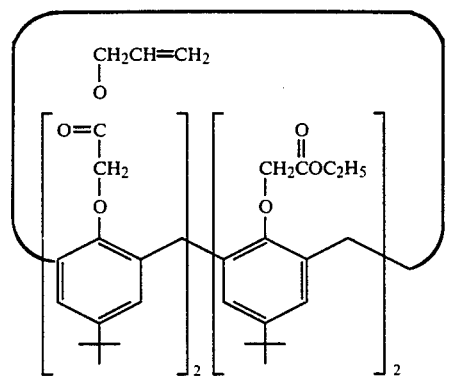

Elemental analysis: (Cald'd for $C_{62}H_{80}O_{12}$, C: 73.18, H: 7.94, O: 18.87; Found C: 73.24, H: 8.14, O: 19.08).

EXAMPLE 4

5,11,17,23-tetra-tert-butyl-25,26,27,28-tetra(2-oxo-2-ethoxy) ethoxy calix[4]arene (1g) is disolved in THF (20 grams) to which dilute HCL is added (2 ml of 5N). The mixture is refluxed for about 45 minutes after which HPLC indicates an approximately 70-80% conversion to diacid. The solvent is removed and the product recrystalized from hot n-hexane repeatedly until substantially pure. The product has the formula:

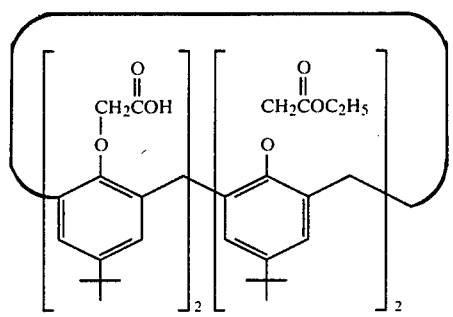

EXAMPLE 5

Ethyl cyanoacrylate stabilized with 10 ppm $BF_3$ was used as a base adhesive formulation. The calixarene compounds listed in Table 1 were disolved in the base adhesive at the indicated levels and fixture times on copy paper and on white deal wood were determined. The results, also shown in Table 1, demonstrate very good accelerative activity for the mixed functional calixarenes.

TABLE 1

| Additive | Amount | Fixture Time Copy Paper | Fixture Time White Deal |
|---|---|---|---|
| None | — | 60 seconds | 5-6 minutes |
| Example 2 | 1% | 5-10 seconds | 1 minute |
| Example 1 | 1% | 10-12 seconds | 1.5-2 minutes |
| Example 4 | 0.5% | 1-3 seconds | 25-30 seconds |
| 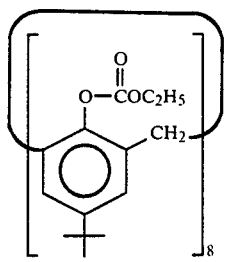 | 1% | — | 3-3.5 minutes |
| 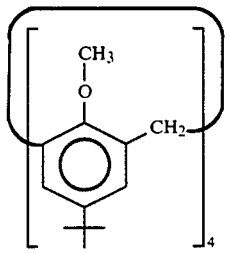 | .2 | greater than 30 seconds | 3-3.5 minutes |
| 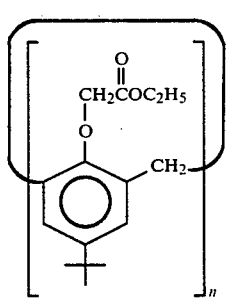 | 1% | less than 1 second | 30 seconds |

We claim:

1. In a cyanacrylate adhesive composition, the improvement comprising that said composition includes an accelerator in a conventional amount, the accelerator being a calixarene compound stable to cyanocrylate monomers represented by the formula:

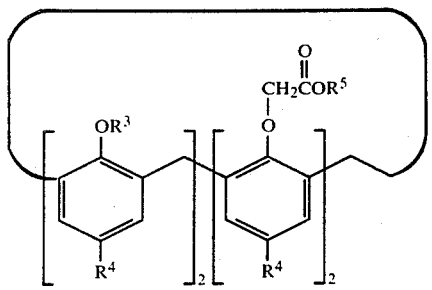

where R³ is H, —CH₂C(=O)OH, —CH₂C(=O)OR⁶, —C(=O)R⁸, hydrocarbyl, or trihydrocarbylsilyl or the two R³ groups together form a divalent hydrocarbyl or oxygen interrupted hydrocarbyl group; R⁴ is H or hydrocarbyl; R⁵ is hydrocarbyl, hydrocarbyl interrupted by one or more oxygen atoms, or hydrocarbyl sustituted with halo, nitro, or oxo groups; R⁶ is as defined for R⁵ but different therefrom; and R⁸ is as defined for R⁵ but the same or different therefrom.

2. The composition of claim 1 wherein R⁵ is CH₂CH₃.

3. The composition of claim 1 wherein R⁴ is selected from H, alkyl and alkenyl.

4. The composition of claim 1 wherein R⁴ is t-butyl.

5. The composition of claim 1 where R³ is selected from H, —CH₂C(=O)OH, and hydrocarbyl and R⁵ is hydrocarbyl.

6. The composition of claim 1 wherein the cyanoacrylate adhesive composition contains a monomer of the formula:

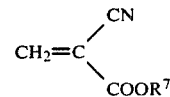

wherein R⁷ represents a substituted or unsubstituted straight chain or branched chain alkyl group having 1 to 12 carbon atoms, a straight chain or branched chain alkenyl group having 2 to 12 carbon atoms, a straight chain or branched chain alkynyl group having 2 to 12 carbon atoms, a cycloalkyl group, an aralkyl group or an aryl group.

7. The composition of claim 1 wherein said calixarene compound is present in the range of 0.1-2% by weight.

8. The composition of claim 1 further comprising an anionic polymerization inhibitor and a free radical polymerization inhibitor.

9. The composition of claim 8 further comprising a thickener.

10. In a method of bonding a pair of substrates comprising applying a cyanoacrylate adhesive to at least one of the substrates and joining the substrates for sufficient time to permit the adhesive to fixture, the improvement comprising that said adhesive includes as an accelerator calixarene compound of claim 1.

11. The method of claim 10 wherein at least one of said substrates is selected from wood, leather, ceramic, plastic and metals with chromate-treated or acidic oxide surfaces.

* * * * *